United States Patent
Luhta et al.

(10) Patent No.: US 6,778,637 B2
(45) Date of Patent: Aug. 17, 2004

(54) METHOD AND APPARATUS FOR ALIGNMENT OF ANTI-SCATTER GRIDS FOR COMPUTED TOMOGRAPHY DETECTOR ARRAYS

(75) Inventors: Randall P. Luhta, Highland Heights, OH (US); William C. Brunnett, Concord, OH (US); Rodney A. Mattson, Mentor, OH (US)

(73) Assignee: Koninklijke Philips Electronics, N.V., Eindhoven (NL)

(*) Notice: Subject to any disclaimer, the term of this patent is extended or adjusted under 35 U.S.C. 154(b) by 22 days.

(21) Appl. No.: 10/251,387

(22) Filed: Sep. 20, 2002

(65) Prior Publication Data

US 2004/0057556 A1 Mar. 25, 2004

(51) Int. Cl.[7] .............................................. G21K 1/02
(52) U.S. Cl. ...................... 378/154; 378/205; 250/363.1
(58) Field of Search ............................... 378/154, 159, 378/145, 205, 4; 250/363.1, 363.02, 363.05, 363.06, 370.11, 370.09

(56) References Cited

U.S. PATENT DOCUMENTS

| | | | |
|---|---|---|---|
| 4,338,521 A | * 7/1982 | Shaw et al. | 250/370.11 |
| 4,429,227 A | * 1/1984 | DiBianca et al. | 250/370.09 |
| 4,607,164 A | * 8/1986 | Kubota et al. | 250/363.02 |
| 5,293,417 A | 3/1994 | Wei et al. | 378/147 |
| 5,357,553 A | 10/1994 | Ferlic et al. | 378/154 |
| 5,487,098 A | * 1/1996 | Dobbs et al. | 378/19 |
| 6,055,296 A | * 4/2000 | Ferlic et al. | 378/154 |
| 6,134,301 A | 10/2000 | Mruzek et al. | 378/147 |

* cited by examiner

Primary Examiner—Edward J. Glick
Assistant Examiner—Hoon Song
(74) Attorney, Agent, or Firm—Fay, Sharpe, Fagan, Minnich & McKee, LLP

(57) ABSTRACT

A radiation detector (30) for a computed tomography scanner (12) includes a support structure (62). An alignment board (60) secures to the support structure (62) and includes photolithographically defined alignment openings (70) arranged to define a spatial focal point (34) relative to the alignment board (60). An anti-scatter element (32) is disposed on the support element (62) and includes one or more protrusions (86) which mate with the alignment openings (70) of the alignment board (60) to align the anti-scatter element (32) with the spatial focal point (34). A detector board (104) includes alignment structures (106) that align the detector board (104) with the anti-scatter element (32).

30 Claims, 15 Drawing Sheets

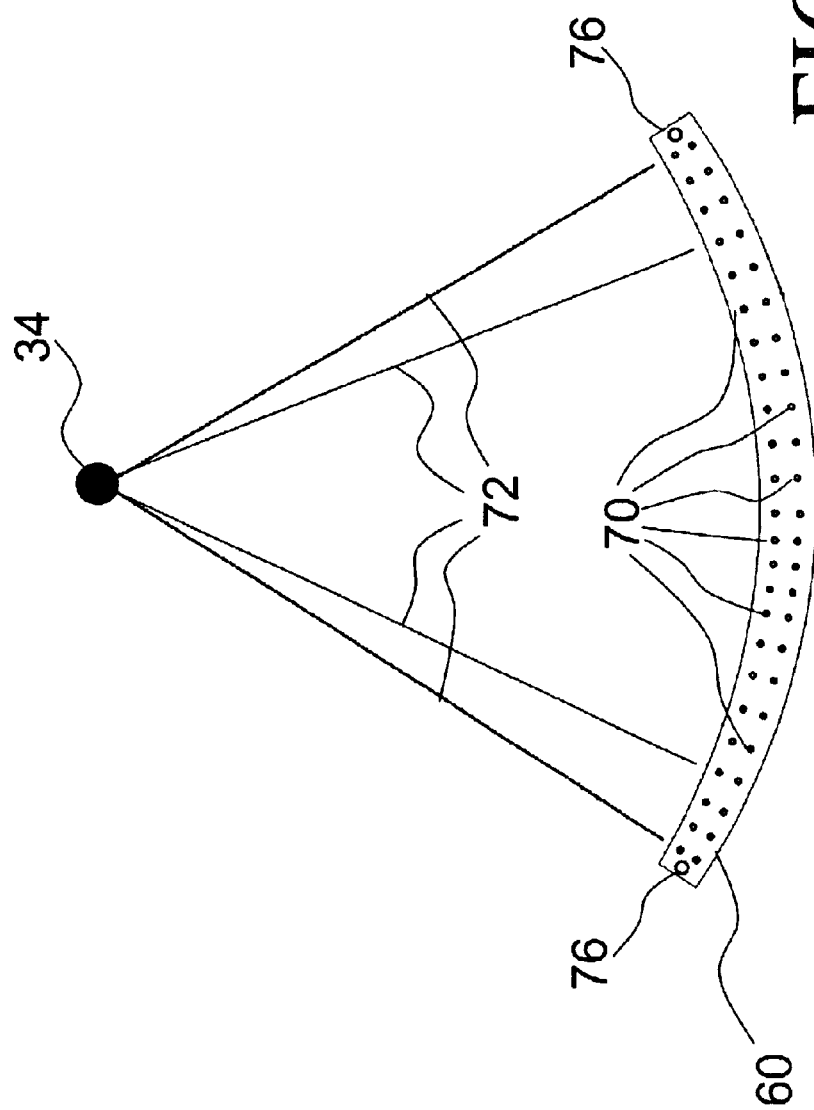

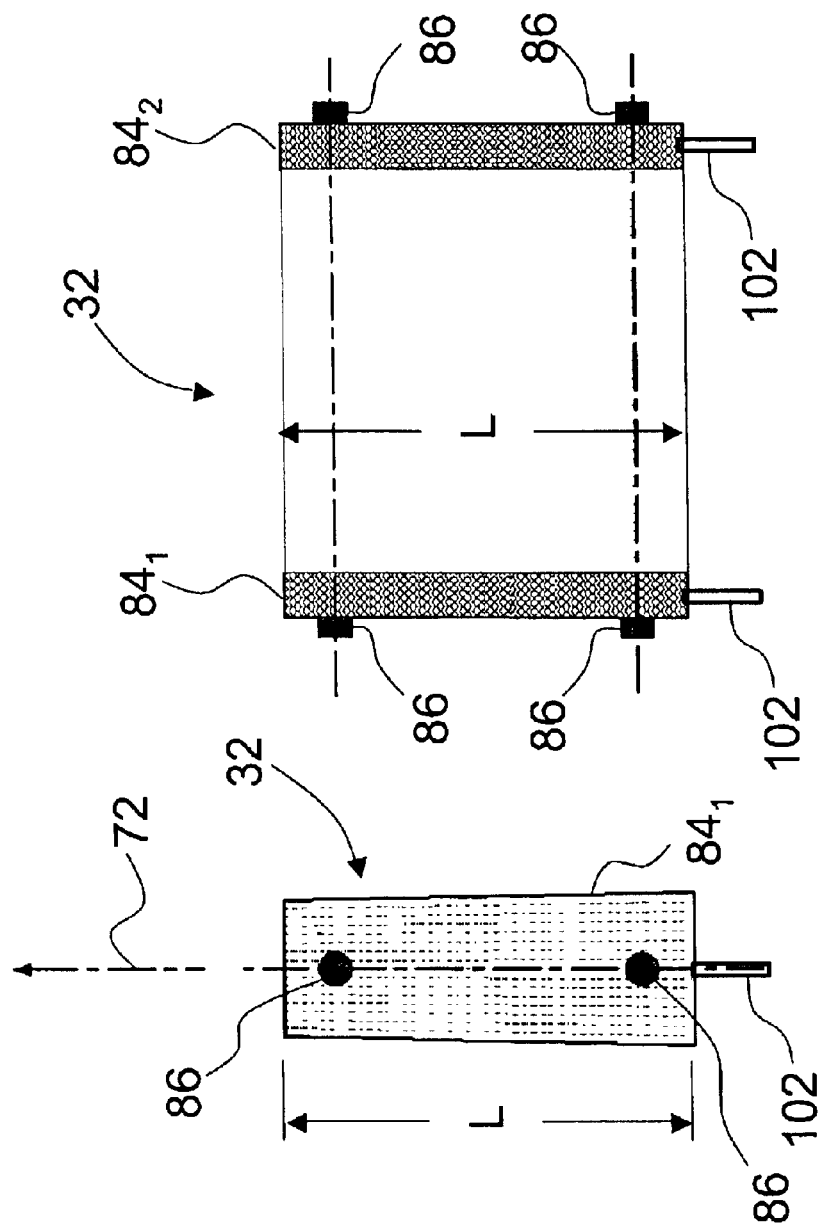

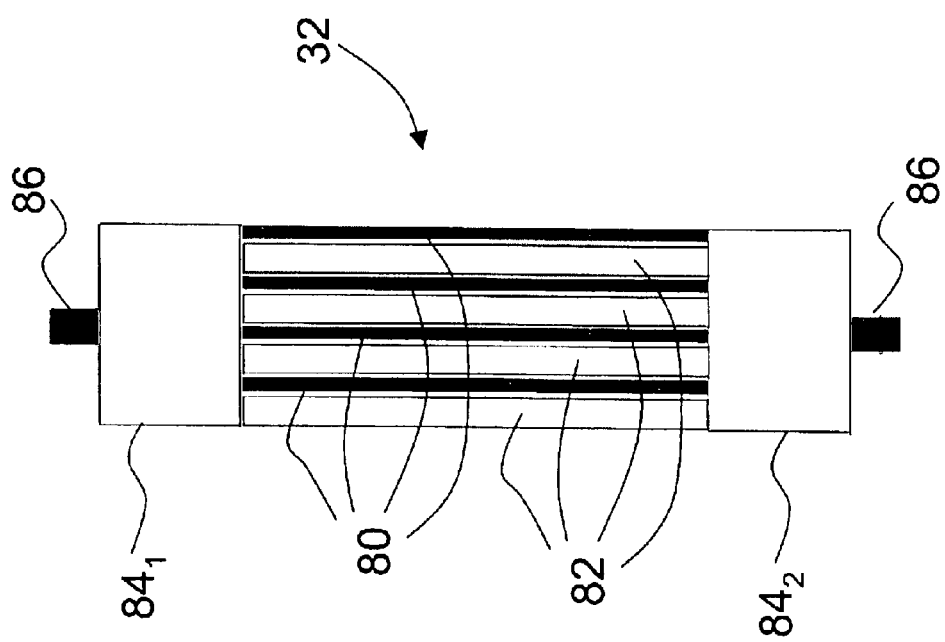

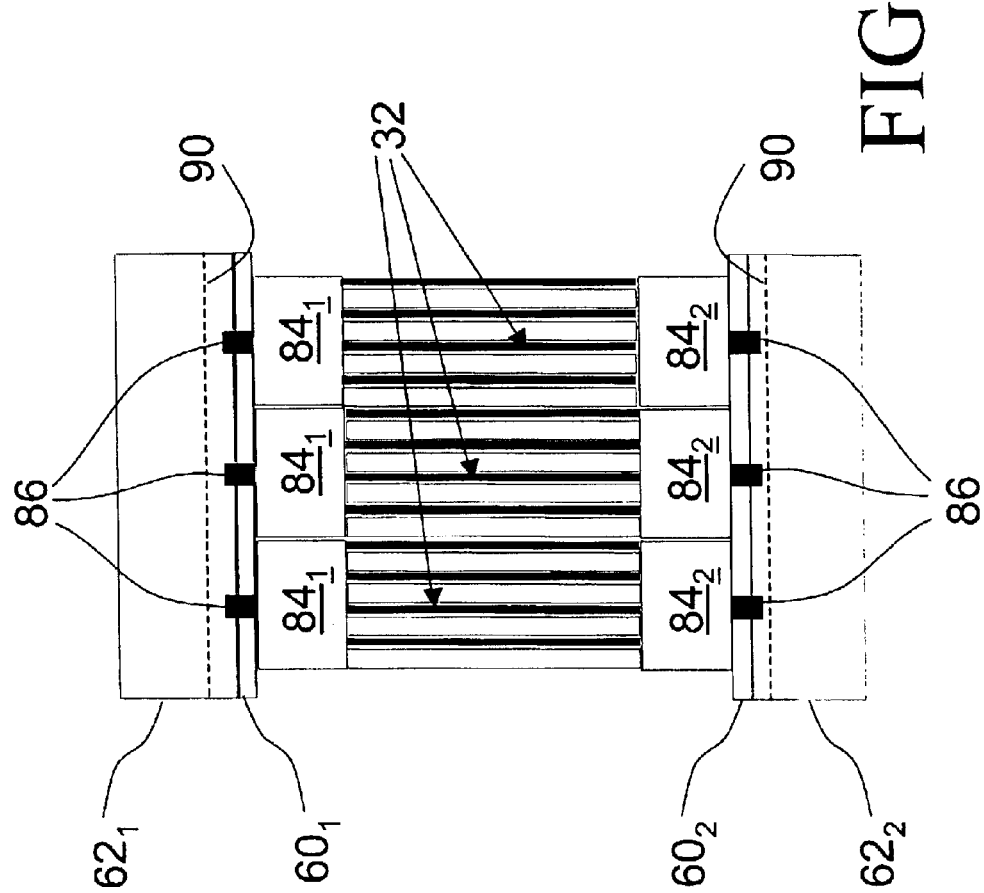

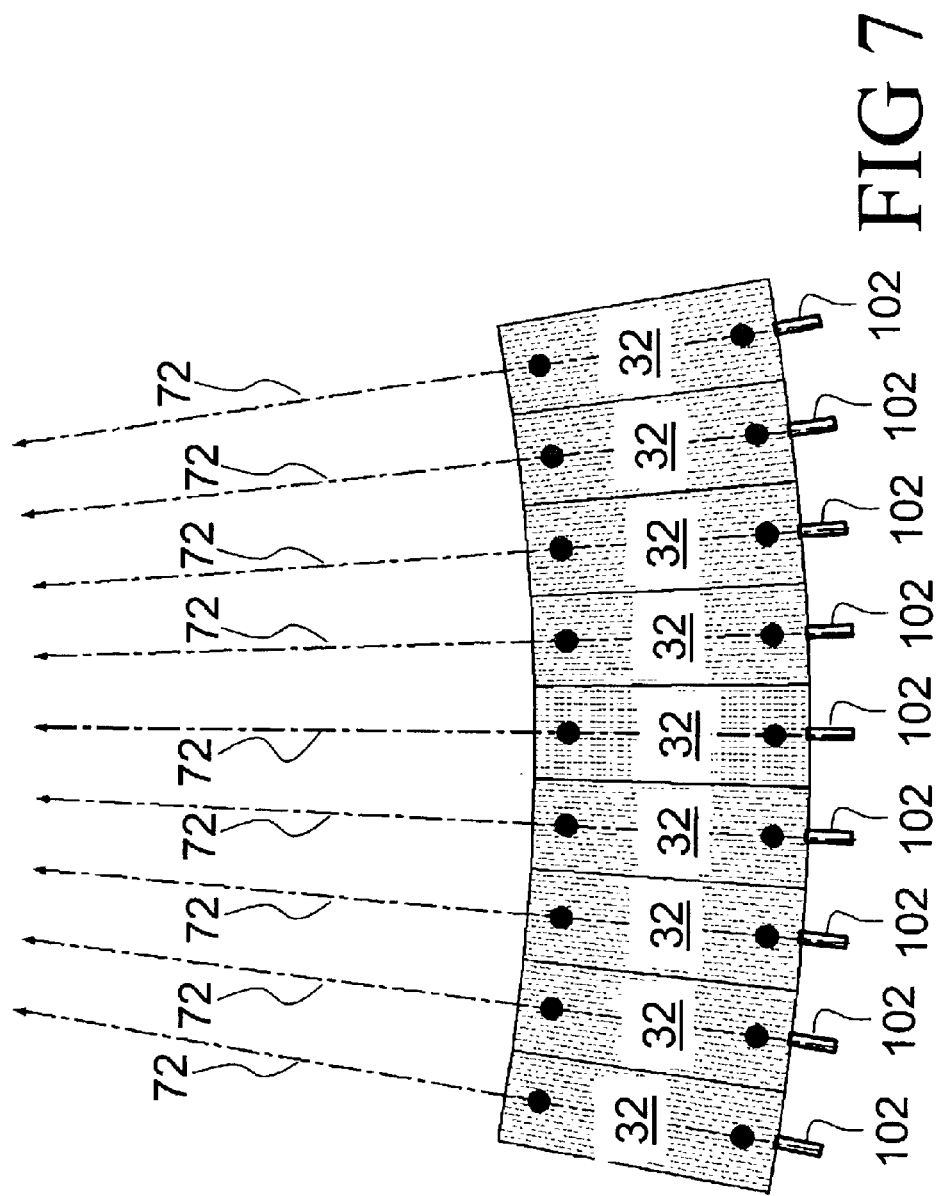

METHOD AND APPARATUS FOR ALIGNMENT OF ANTI-SCATTER GRIDS FOR COMPUTED TOMOGRAPHY DETECTOR ARRAYS

BACKGROUND OF THE INVENTION

The present invention relates to the diagnostic imaging arts. It particularly relates to computed tomography imaging employing an x-ray source and a two-dimensional detector array that enables rapid acquisition of volumetric x-ray absorption imaging data, and will be described with particular reference thereto. However, the invention will also find application in other types of radiation detectors for a variety of imaging applications employing x-rays, visible light, radiation from an administered radiopharmaceutical, or other types of radiation. The invention will further find application in non-imaging radiation detectors.

Computed tomography (CT) imaging typically employs an x-ray source that generates a fan-beam, wedge-beam, or cone-beam of x-rays that traverse an examination region. A subject arranged in the examination region interacts with and absorbs a portion of the traversing x-rays. A one- or two-dimensional radiation detector including an array of detector elements is arranged opposite the x-ray source to detect and measure intensities of the transmitted x-rays.

Typically, the x-ray source and the radiation detector are mounted at opposite sides of a rotating gantry such that the gantry is rotated to obtain an angular range of projection views of the subject. In some configurations the x-ray source is mounted on the rotating gantry while the radiation detector is mounted on a stationary gantry. In either configuration, the projection views are reconstructed using filtered back-projection or another reconstruction method to produce a three-dimensional image representation of the subject or of a selected portion thereof. Typically, the reconstruction assumes that the radiation traversed a linear path from the x-ray source directly to the detector. Any scattered radiation that reaches the detector degrades the resultant image.

The detector array of the radiation detector typically includes a scintillator crystal array which produces bursts of light, called scintillation events, in response to x-rays. A two-dimensional array of photodetectors such as a monolithic silicon photodiode array are arranged to view the scintillator and produce analog electrical signals indicative of the spatial location and intensity of the scintillation event. The intensity is typically translatable into an energy of the x-ray photon that produced the scintillation event, and hence provides spectral information.

Typically, the detector array is a focus-centered array including a curved detection surface defining a focus that coincides with a focus of the x-ray beam which is typically at or near the x-ray source. Preferably, anti-scatter elements such as arrays of anti-scatter plates are mounted in front of the scintillator, and are precisely aligned with the x-ray paths to block scattered x-rays which would otherwise contribute to measurement noise. The spacing between the anti-scattering plates defines slits through which the direct or non-scattered x-rays pass unimpeded. However, scattered x-rays are angularly deviated due to the scattering and strike the anti-scatter plates which absorb the scattered x-rays.

The anti-scatter plates are preferably thin to minimize absorption of direct x-rays, and tall in the direction of the x-ray source to maximize absorption of scattered x-rays having small deviation angles. The degree of scatter rejection is improved by using plates constructed from a metal or other material with a high atomic number and by making the plates tall in the direction pointing toward the focal spot of the focus-centered detector array. In present anti-scatter elements, plates with heights of between one centimeter and four centimeters are typical.

These large anti-scatter plate heights require precise alignment of the anti-scatter elements with the spatial focal point of the detector array, and similarly precise alignment of the x-ray source at the spatial focal point. Misalignment of the anti-scatter plates can produce shadowing of the detectors by the anti-scatter plates. Shadowing, in turn, leads to reduced x-ray intensities and image artifacts which generally manifest as rings in the image reconstruction. Spatially non-uniform shadowing also leads to spectral differences in the detected x-rays and non-linear detector array characteristics. Furthermore, if the anti-scatter plates are inadequately secured, mechanical vibrations can produce temporally varying shadowing due to mechanical flexing of the tall, thin anti-scatter plates during gantry rotation which leads to a variety of image artifacts.

A conventional detector array is assembled starting with the radiation detectors, which are commonly monolithic photodiode arrays. The photodiode arrays are mounted to ceramic support substrates for rigidity, and scintillator crystals are bonded to the monolithic photodiode arrays to form detector boards. Anti-scatter elements are next mounted and aligned with the photodiodes on the detector boards. The detector boards with joined anti-scatter elements are mounted onto a mechanical base plate and manually aligned with a spatial focal spot corresponding to a convergence point of the x-ray beam. Mounting brackets for mounting the radiation detector onto the computed tomography imaging scanner are also connected to the base plate. Finally, the radiation detector is mounted onto the computed tomography scanner.

A common problem in such detector arrays is cumulative alignment stack-up errors. Accumulation of errors in alignment of the photodiode arrays, the scintillators, and the anti-scatter elements, followed by further alignment errors introduced in mounting the detector boards onto the mechanical base plate, can lead to substantial cumulative misalignment of the anti-scatter plates relative to the x-ray beam. Usually, shims, spacers, or other mechanical adjustments are provided for precisely adjusting the alignment of the anti-scatter plates of the constructed and mounted radiation detector to correct the misalignment. These mechanical adjustments are time-consuming, and the alignment accuracy of the final array is dependent upon the skill of the individual performing the anti-scatter plate adjustments.

The present invention contemplates an improved apparatus and method that overcomes the aforementioned limitations and others.

SUMMARY OF THE INVENTION

According to one aspect of the invention, a two-dimensional radiation detector is disclosed for a radiographic scanner. A support structure is provided. An alignment board secures to the support structure and includes alignment openings arranged to define a spatial focus relative to the alignment board. An anti-scatter module is disposed on the support element and includes one or more protrusions which mate with the alignment openings of the alignment board to align the anti-scatter module with the spatial focus. A detector board is provided, including a substrate and an array of radiation-sensitive elements arranged on the substrate for detecting radiation produced by the radiographic scanner. The detector board further includes alignment structures that align the detector board with the anti-scatter module.

According to another aspect of the invention, a method is provided for manufacturing a radiation detector for a computed tomography scanner. Alignment openings are defined in an alignment board. An anti-scatter element is aligned with the alignment board by mating one or more protrusions of the anti-scatter element with a selected one or more of the alignment openings of the alignment board. A detector board is aligned and mounted with the anti-scatter element. The detector board includes a substrate and an array of radiation-sensitive elements arranged thereon.

According to yet another aspect of the invention, a radiographic scanner is disclosed. A radiation source is mounted to a support frame. The radiation source emits a diverging radiation beam from a focal region. First and second generally symmetrical, substantially planar alignment boards are arranged parallel to one another and secured to the support frame. Each alignment board includes an array of alignment openings formed therein. A plurality of anti-scatter plates are arranged between the alignment boards and aligned with respect to the radiation focal region by couplings to alignment openings of both the first and the second alignment boards. A plurality of detector boards align with the anti-scatter plates.

One advantage of the present invention resides in a substantial reduction in stack-up errors in the alignment of the anti-scatter elements.

Another advantage of the present invention resides in improved accuracy in alignment of anti-scatter plates or elements.

Another advantage of the present invention resides in an improved method for manufacturing highly precise and accurate alignment plates for radiation detectors which is readily scaled to higher densities of alignment openings of various shapes and sizes.

Yet another advantage of the present invention resides in a simplified process for assembling a detector array for computed tomography imaging.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

FIG. 4 schematically shows a side view of an exemplary alignment plate according to an embodiment of the invention, with radial lines showing alignment relationships between alignment opening pairs and a spatial focal point of the radiation detector.

FIG. 5A shows an end view of a first embodiment of an anti-scatter element or module of the radiation detector of FIG. 1.

FIG. 5B shows a side view of the anti-scatter element or module of FIG. 5A.

FIG. 5C shows a top view from the direction of the focal spot of the anti-scatter element or module of FIGS. 5A and 5B.

FIG. 6 shows three anti-scatter elements of the type shown in FIGS. 5A, 5B, and 5C mounted in the radiation detector of FIG. 1.

FIG. 7 schematically shows several anti-scatter elements of the type shown in FIGS. 5A, 5B, and 5C mounted in the radiation detector of FIG. 1, with radial lines shown that connect alignment protrusions of the anti-scatter modules with the spatial focal point of the radiation detector.

DETAILED DESCRIPTION OF THE PREFERRED EMBODIMENTS

Figure 1:
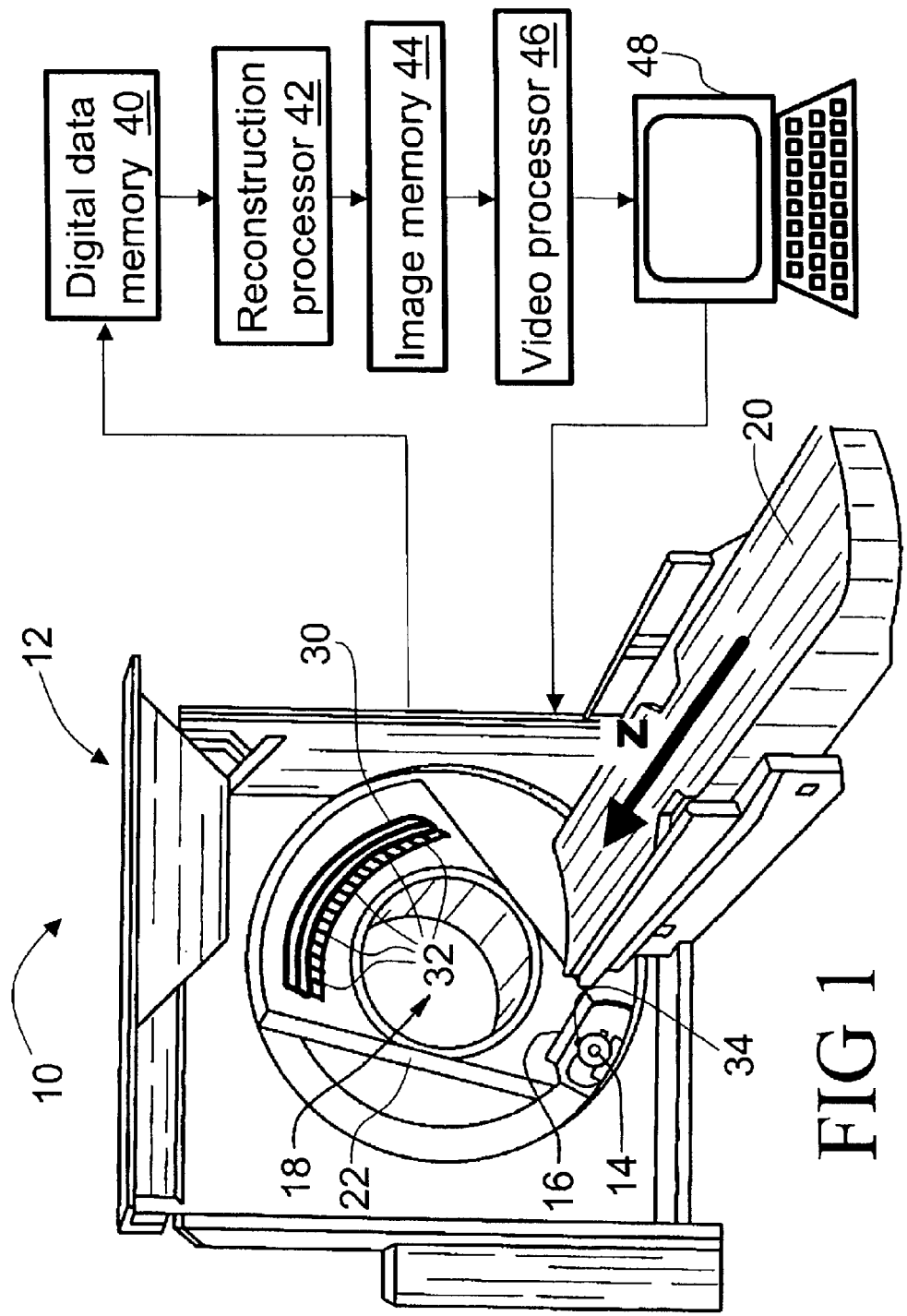
FIG. 1 shows an exemplary computed tomography imaging apparatus employing a radiation detector constructed in accordance with one embodiment of the invention.

With reference to FIG. 1, a computed tomography (CT) imaging apparatus or CT scanner 10 includes a gantry 12. An x-ray source 14 and a source collimator 16 cooperate to produce a fan-shaped, cone-shaped, wedge-shaped, or otherwise-shaped x-ray beam directed into an examination region 18 which contains a subject (not shown) such as a patient arranged on a subject support 20. The subject support 20 is linearly movable in a Z-direction while the x-ray source 14 on a rotating gantry 22 rotates around the Z-axis.

In an exemplary helical imaging mode, the rotating gantry 22 rotates simultaneously with linear advancement of the subject support 20 to produce a generally helical trajectory of the x-ray source 14 and collimator 16 about the examination region 18. However, other imaging modes can also be employed, such as a single- or multi-slice imaging mode in which the gantry 22 rotates as the subject support 20 remains stationary to produce a generally circular trajectory of the x-ray source 14 over which an axial image is acquired. After the axial image is acquired, the subject support optionally steps a pre-determined distance in the Z-direction and the axial image acquisition is repeated to acquire volumetric data in discrete steps along the Z-direction.

A radiation detector 30 is arranged on the gantry 22 across from the x-ray source 14. In the exemplary CT scanner 12, the radiation detector 30 spans a selected angular range that preferably comports with a fan angle of the x-ray beam. The radiation detector 30 includes several rows of detectors along the Z-direction for acquiring imaging data along a portion of the Z-direction in each projection view. The radiation detector 30 is arranged on the gantry 22 opposite to the x-ray source 14 and rotates therewith so that the radiation detector 30 receives x-rays that traverse the examination region 14 as the gantry 22 rotates.

A plurality of anti-scatter elements 32, such as spaced anti-scatter plates, are arranged on the radiation detector 30 and are oriented with respect to a spatial focal point 34 generally corresponding to an origin or convergence point of the x-ray beam. The spatial focal point 34 is typically on the anode of the x-ray source 14. The detector 30 is a focus-centered detector centered on the spatial focal point 34.

Instead of the arrangement shown in FIG. 1, it is also contemplated to arrange the radiation detector on a stationary portion of the gantry encircling the rotating gantry such that the x-rays continuously impinge upon a continuously shifting portion of the radiation detector during source rotation.

With continuing reference to FIG. 1, the gantry 22 and the subject support 20 cooperate to obtain selected projection views of the subject along a helical trajectory or other trajectory of the x-ray source 14 relative to the subject. The path of the x-ray source 14 preferably provides substantial angular coverage for each voxel of the imaged region of interest to reduce image artifacts. Projection data collected by the radiation detector 30 are communicated to a digital data memory 40 for storage.

A reconstruction processor 42 reconstructs the acquired projection data, using filtered backprojection, an n-PI reconstruction method, or other reconstruction method, to generate a three-dimensional image representation of the subject or of a selected portion thereof which is stored in an image memory 44. The image representation is rendered or otherwise manipulated by a video processor 46 to produce a human-viewable image that is displayed on a graphical user interface (GUI) 48 or another display device, printing device, or the like for viewing by an operator.

Preferably, the GUI 48 is additionally programmed to interface a human operator with the CT scanner 12 to allow the operator to initialize, execute, and control CT imaging sessions. The GUI 48 is optionally interfaced with a communication network such as a hospital or clinic information network via which image reconstructions are transmitted to medical personnel, a patient information database is accessed, or the like.

Figure 2:
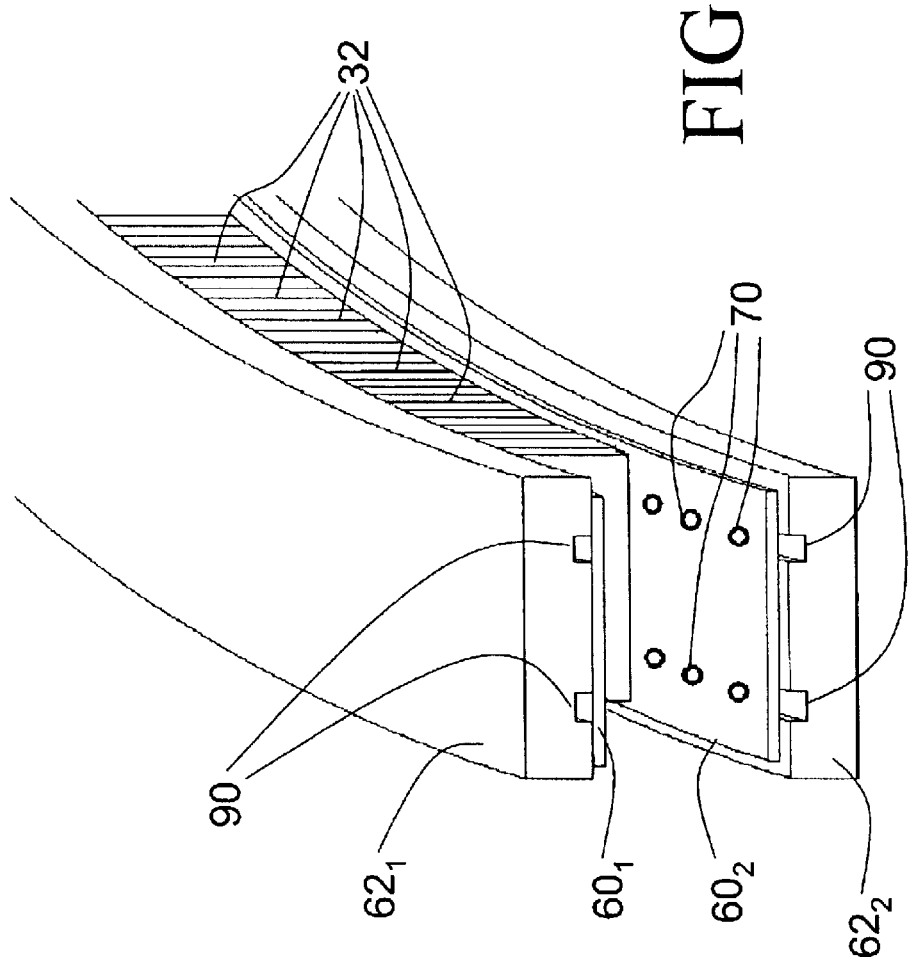
FIG. 2 shows a perspective view of the anti-scatter grid of the radiation detector of FIG. 1.

With continuing reference to FIG. 1 and with further reference to FIG. 2, the anti-scatter elements 32 are arranged between first and second generally symmetrical, substantially planar, alignment plates or boards $60_1$, $60_2$. The alignment plates $60_1$, $60_2$ are preferably arranged in a large arc, generally parallel to one another. The alignment plates $60_1$, $60_2$ are thin metallic plates, preferably made of a corrosion-resistant metal, such as stainless steel, which are supported by corresponding rigid support elements $62_1$, $62_2$, respectively. Preferably, the support elements $62_1$, $62_2$ are components or cast portions of a detector support frame that mechanically supports, secures, and/or retains functional components of the radiation detector 30 including the anti-scatter elements 32.

Figure 3:
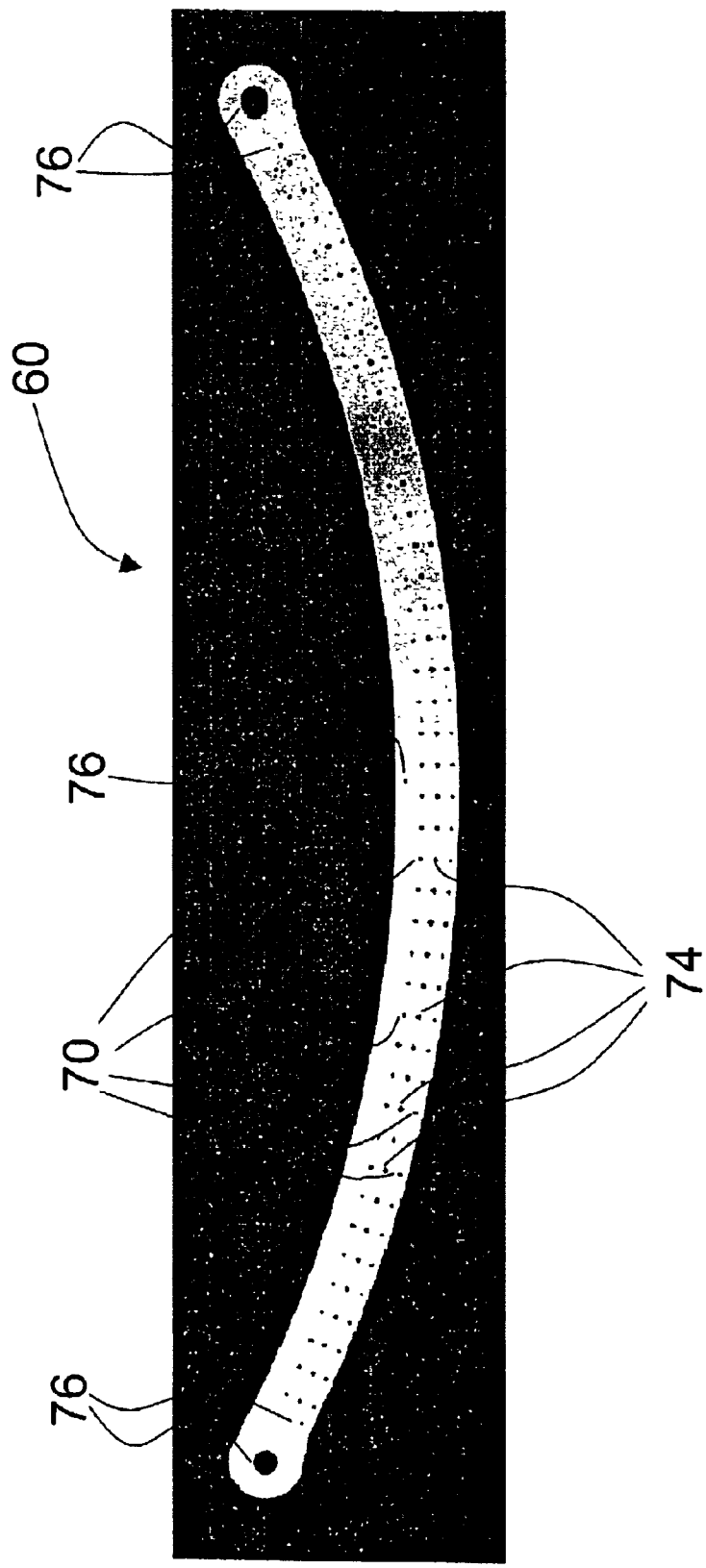
FIG. 3 shows a side view of an alignment plate for the radiation detector of FIGS. 1 and 2.

With continuing reference to FIG. 2 and with further reference to FIGS. 3 and 4, each alignment plate $60_1$, $60_2$, numbered generally as 60, includes a plurality of anti-scatter element alignment openings 70 formed therein. As shown in FIG. 4, the anti-scatter element module alignment openings 70 are arranged in pairs along radial lines 72 that converge at the spatial focal spot 34 which coincides with the x-ray source 14 or a convergence of the fan-shaped, cone-shaped, wedge-shaped, or otherwise-shaped x-ray beam produced by the cooperating x-ray source 14 and source collimator 16. In FIG. 4, a few exemplary radial lines 72 are shown to indicate the alignment of pairs of anti-scatter element alignment openings 70 with the spatial focal point 34.

In the embodiment of the alignment plate 60 shown in FIG. 3, an additional opening 74 is arranged between each pair of anti-scatter element alignment openings 70. The extra opening 70 is preferably aligned along the radial line 72 of the pair of anti-scatter element alignment openings 70, and provides a pass-through for a fastener that secures the anti-scatter element or module 32 to the rigid support element 62. Further additional alignment openings 76 in the alignment plates 60 are optionally included to align the alignment plates 60 with the support elements $62_1$, $62_2$ or to align other elements of the radiation detector 30.

With continuing reference to FIGS. 2–4 and with further reference to FIGS. 5A, 5B, and 5C, the anti-scatter elements or modules 32 each include a plurality of anti-scatter plates or vanes 80 arranged generally in conformity with the rays or planes 72 and separated by spacer plates 82 that are generally parallel to the anti-scatter plates 80 and define a selected spacing and convergence angle between anti-scatter plates 80. The non-scattered radiation is directed parallel to the anti-scatter plates 80 and pass therebetween, while scattered radiation angularly deviates from parallel with the anti-scatter plates 80 and is typically absorbed by the anti-scatter plates 80.

Although the anti-scatter plates or vanes 80 are generally parallel to one another, those skilled in the art will recognize that precisely parallel plates do not exactly align with the spatial focal point 34. That is, precisely parallel planes do not contain any points in common, and hence cannot contain the spatial focal point 34 in common. Preferably, the generally parallel anti-scatter plates or vanes 80 are each aligned with a plane that intersects the spatial focal point 34. Such planes are close to, but not exactly, parallel over a length L of the anti-scatter plate 80 since L is short compared a distance between the anti-scatter module 32 and the spatial focal point 34.

In a preferred embodiment for obtaining the preferred generally parallel arrangement of anti-scatter plates 80 in the module 32, the sides of the spacer plates 82 that contact the anti-scatter plates 80 are preferably slightly non-parallel. An angle of the non-parallel sides is selected to provide a slight tilt of the contacting anti-scatter plates 80 relative to one another to closely align each anti-scatter plate 80 with a plane that intersects the spatial focal point 34.

The anti-scatter plates or vanes 80 are preferably formed of a material with a high atomic number that is highly absorbing for radiation produced by the x-ray source 14, such as tantalum, tungsten, lead, or the like. The spacer plates 82 are formed of a material that is substantially translucent to radiation produced by the x-ray source 14, and are suitably formed of a plastic material. In a preferred embodiment, the spacer plates 82 are substantially hollow molded plastic frames, rather than full molded plastic slabs, to further reduce radiation absorption in the spacer plates 82.

The arrangement of generally parallel anti-scatter plates 80 and spacer plates 82 is secured at the sides by two end caps $84_1$, $84_2$. Each end cap 84 includes alignment pins or other alignment protrusions 86 that are aligned along the radial line or plane 72, as best seen in FIG. 5A. In a preferred embodiment, the protrusions 86 of one end cap $84_2$, align with the protrusions 86 of the other end cap $84_2$, as best seen in FIG. 5B, so that the two end caps $84_1$, $84_2$ are interchangeable. Optionally, an adhesive such as a pressure-sensitive adhesive is disposed between contacting surfaces of the anti-scatter plates 80 and the spacer plates 82 to provide additional structural support.

With continuing reference to FIGS. 2–5C and with further reference to FIGS. 6 and 7, the alignment protrusions 86 of the anti-scatter modules 32 mate with the anti-scatter alignment openings 70 of the alignment plates $60_1$, $60_2$ to align the anti-scatter modules 32 with the spatial focal point 34. Because both the openings and the protrusions are defined with precision, the modules are precisely aligned upon insertion. No adjustment in the alignment is necessary. As best seen in FIGS. 2 and 6, the rigid support elements $62_1$, $62_2$ include recess troughs 90 aligned with the anti-scatter alignment openings 70 that provide space for the protrusions 86 to pass through the alignment openings 70. The recess troughs 90 do not provide precise alignment and hence need not be formed with close tolerances.

In the preferred illustrated embodiment the two alignment plates $60_1$, $60_2$ cooperate in aligning the anti-scatter modules 32. However, it is also contemplated to employ only a single alignment plate 60.

Figure 8:
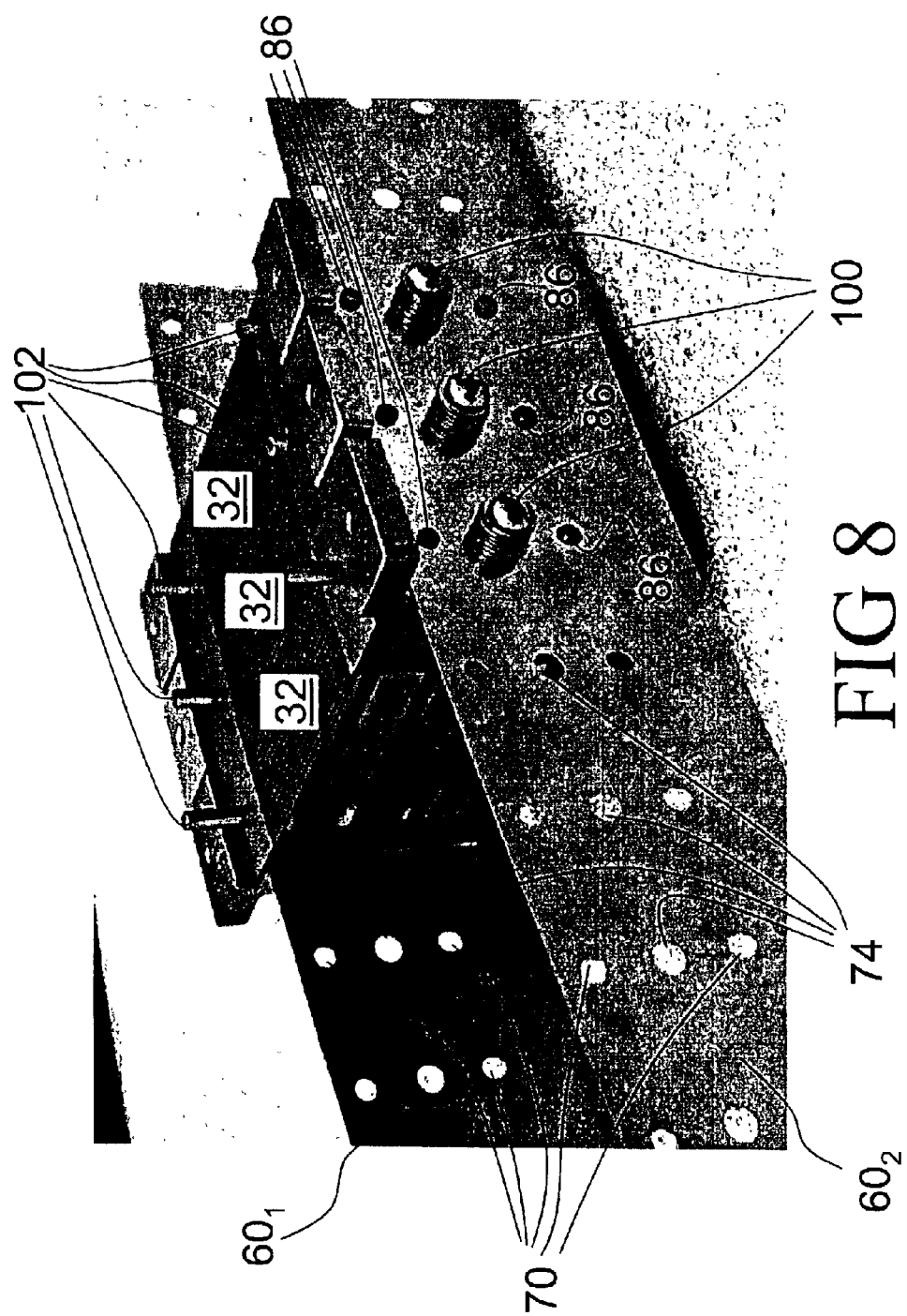
FIG. 8 shows a perspective view of a portion of an anti-scatter grid with three mounted anti-scatter modules of the type shown in FIGS. 5A, 5B, and 5C.
Figure 9:
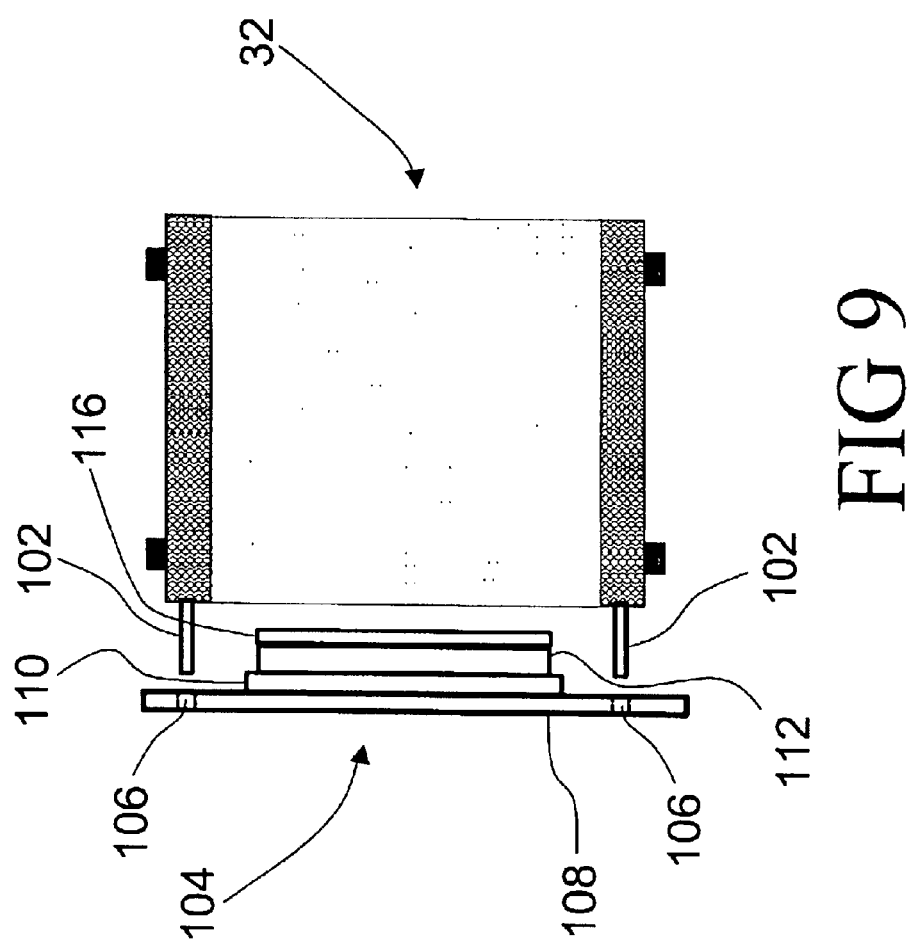
FIG. 9 shows a side view of the anti-scatter elements shown in FIGS. 5A, 5B, and 5C along with an exploded connection of a detector array module that aligns thereto.

With reference to FIGS. 8 and 9, the anti-scatter elements 32 are aligned using the alignment protrusions 86 and fastened in the radiation detector 30 using threaded fasteners 100 that pass through the openings 74. It should be noted that in FIG. 8, the side that faces the x-ray tube 14 is facing down. Although in FIG. 8 the support elements $62_1$, $62_2$ are omitted to show the alignment openings 70, 74, the fasteners 100 preferably secure to the support elements $62_1$, $62_2$. Additional protrusions or pins 102 preferably extend from a backside of each anti-scatter module 32 to provide alignment for photodetector array modules 104 that align with the anti-scatter modules 32. The pins 102 of each anti-scatter module 32 precisely mate with precision openings 106 of a corresponding photodetector array module 104 to provide alignment of the photodetector array module 104 with its corresponding anti-scatter module 32.

Figure 10:
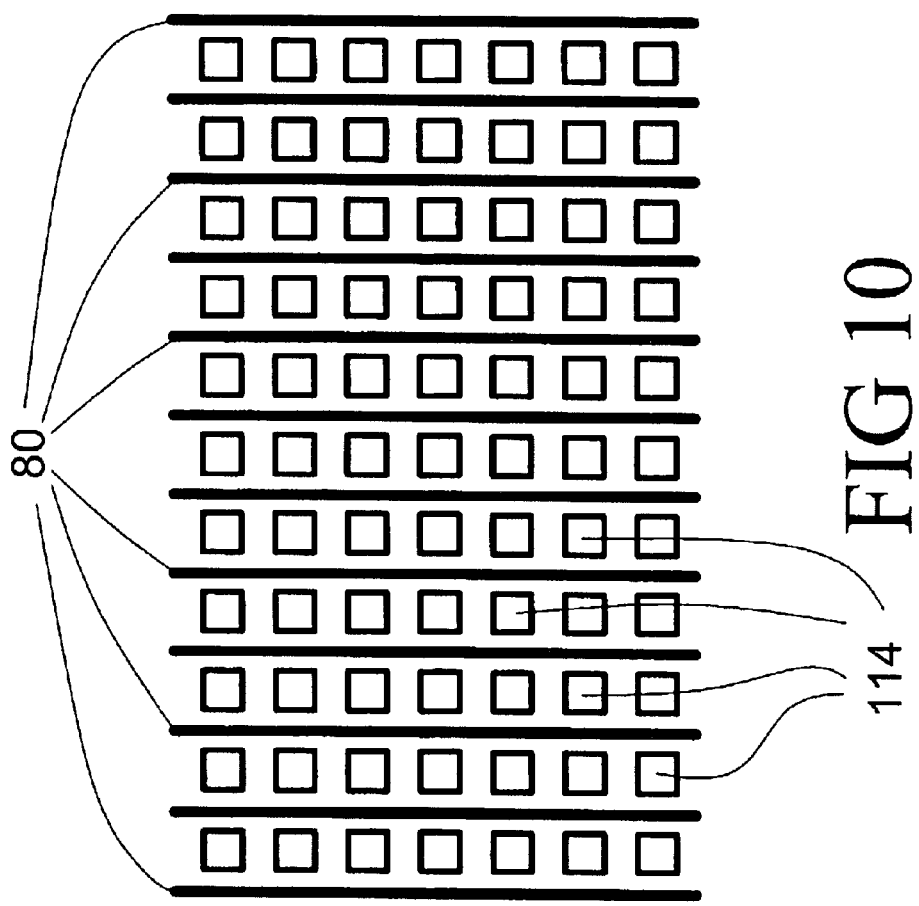
FIG. 10 schematically shows alignment of the detector elements of the detector array module of FIG. 9 between anti-scatter plates of the anti-scatter element.

With continuing reference to FIG. 9 and with further reference to FIG. 10, each photodetector array module 104 includes a substrate 108 on which is disposed a photodetector array 110. A scintillator layer or array 112 is disposed on the photodetector array 110 to provide conversion of x-rays to light that is detectable by the photodetector array 110. The photodetector array 110 is preferably a monolithic array of silicon photodiodes, amorphous silicon, charge-coupled devices, or other semiconductor photodetectors that is divided into individual detector elements 114 by wafer-level photolithographic processing of the monolithic photodiode array, by a mask 116 of tungsten or other x-ray absorbing material, or by a combination of processing and masking.

The alignment of the photodetector array module 104 to the anti-scatter module 32 arranges the detector elements 114 in the gaps between the anti-scatter plates 80 as shown in FIG. 10. The detector elements 114 view between the anti-scatter plates 80, i.e. view through the spacer plates 82 such that scattered radiation which angularly deviates from the unscattered radiation is substantially absorbed by the anti-scatter plates 80 and does not reach the detector elements 114.

Figure 11:
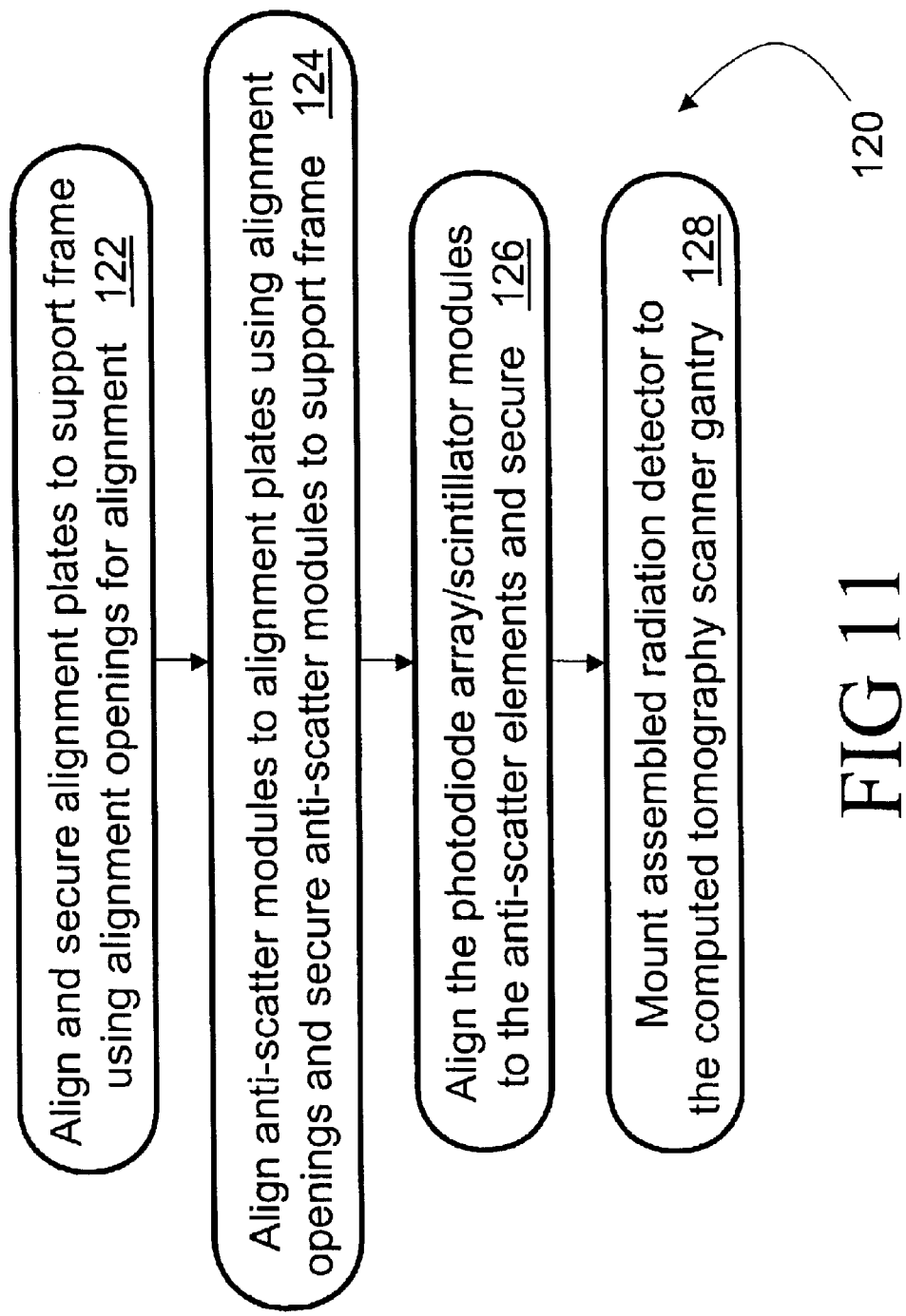
FIG. 11 shows a preferred method for assembling and mounting the radiation detector shown in FIG. 1.

With continuing reference to FIGS. 1–10 and with further reference to FIG. 11, a preferred method 120 for assembling the radiation detector 30 is described. In a step 122, the alignment plates $60_1$, $60_2$ are aligned onto the corresponding support elements $62_1$, $62_2$ using at least some of the additional alignment openings 76, and are secured thereto, e.g. using fasteners that pass through selected openings 76.

In a step 124, the anti-scatter elements or modules 32 are aligned with the anti-scatter alignment openings 70 by coupling the alignment projections 86 with the anti-scatter alignment openings 70 of the alignment plates $60_1$, $60_2$, and the anti-scatter modules 32 are secured to the support elements $62_1$, $62_2$ using the fasteners 100. In a step 126, each photodetector array module 104 is aligned to each corresponding anti-scatter module 32 using the mating alignment pins 102 and openings 106, and the photodetector array module 104 is secured to the anti-scatter module 32, the support elements 62, or another suitable support.

It will be appreciated that if the photodetector array modules 104 are secured to corresponding anti-scatter modules 32, then the alignment steps 124, 126 are optionally reversed. That is, the step 126 of aligning the photodetector array modules 104 to the anti-scatter modules 32 can be performed first, with each photodetector array module 104 aligned and secured to a corresponding anti-scatter module 32, followed by alignment of the anti-scatter modules 32 with attached photodetector array modules 104 to the alignment plates 60 in the step 124.

In a step 128, the assembled radiation detector 30 is aligned and mounted to the computed tomography scanner gantry 22. The aligned anti-scatter modules 32 of the radiation detector 30 cooperatively define a spatial focal spot 34, as best seen in FIGS. 4, 5A, and 7. The radiation detector 30 is aligned on the rotating gantry 22 such that the spatial focal spot 34 coincides with a spatial convergence of the rays of the x-ray cone-, wedge-, or otherwise-shaped beam produced by the cooperating x-ray source 14 and source collimator 16. Alternatively, in the step 128 the x-ray source 14 and the source collimator 16 are aligned with respect to the spatial focal spot 34 associated with the radiation detector 30.

The assembly method 120 described with particular reference to FIG. 11 relies upon the alignment plates $60_1$, $60_2$ accurately and precisely defining the alignment of the anti-scatter modules 32 through the anti-scatter alignment openings 70. The support elements $62_1$, $62_2$ similarly are aligned with respect to the alignment plates $60_1$, $60_2$ using at least some of the additional alignment openings 76.

The alignment openings 70, 76 are precisely and accurately positioned. Furthermore, for manufacturing purposes, the alignment plates $60_1$, $60_2$ are preferably mass-produced with close tolerances in the positioning and sizing of the alignment openings 70, 76. In a preferred embodiment, the alignment plates $60_1$, $60_2$ are interchangeable, so that a single part is mass-produced for manufacturing quantities of the radiation detector 30.

Figure 12:
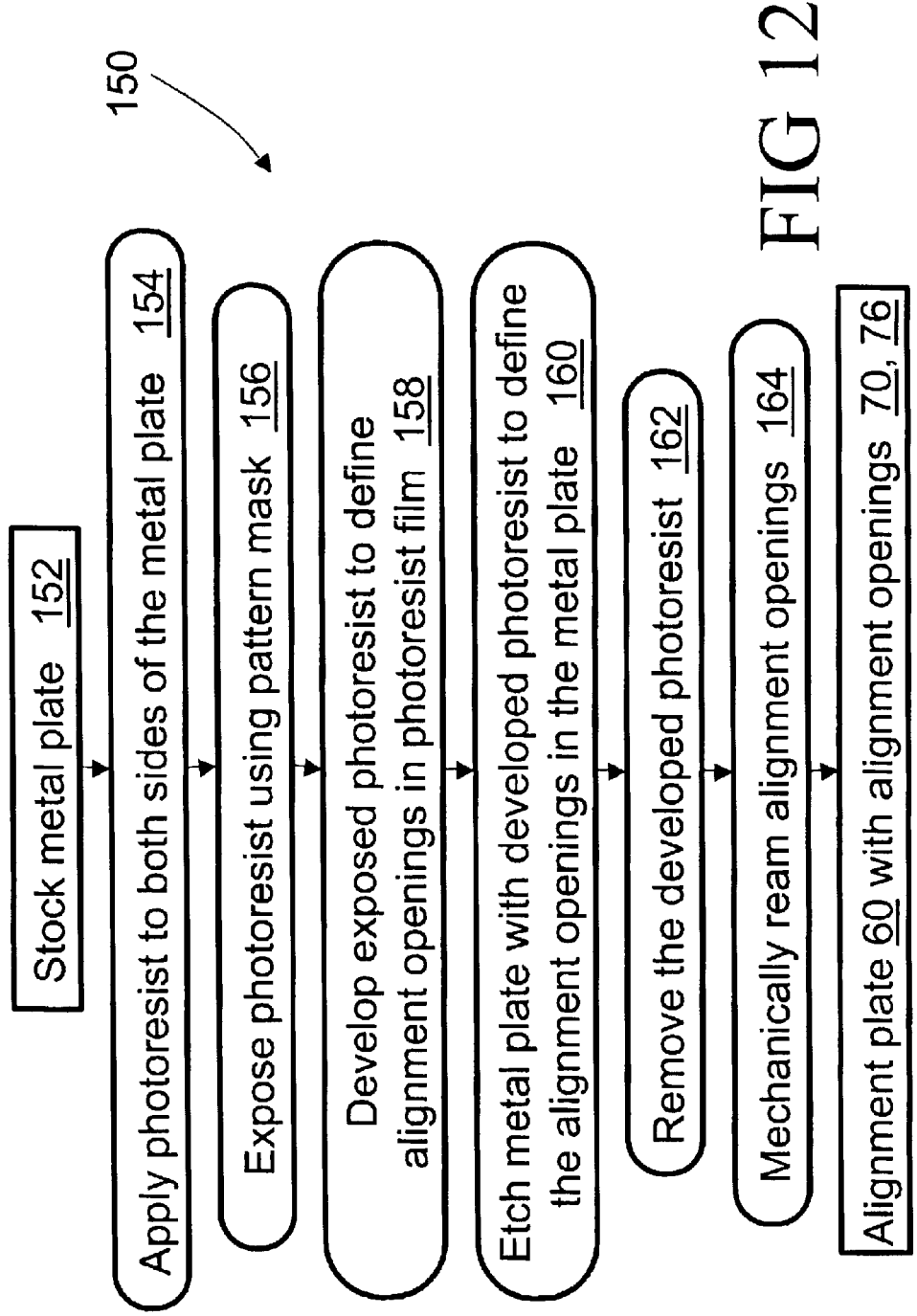
FIG. 12 shows a preferred photolithographic method for fabricating radiation detector alignment plates.

With reference to FIG. 12, a preferred photolithographic method 150 for manufacturing the alignment plate 60 is described. The method 150 operates on a stock metal plate 152, which is preferably thin (e.g., about 0.025 cm thick) and cut to at least approximately correspond to the desired lateral dimensions of the alignment plate 60. The stock metal plate 152 is preferably a stainless steel plate which is advantageously strong and corrosion-resistant. However, an aluminum alloy or other material can also be used.

In one suitable embodiment, the stock metal plate 152 is cut mechanically to define the shape of the alignment plate 60. In a preferred embodiment, however, the mechanical cutting of the stock metal plate is limited to defining a rectangular or other regular shape whose dimensions exceed the outer dimensions of the desired alignment plate 60. In this latter embodiment, the photolithographic method 150 described below precisely defines the outer dimensions of the alignment plate simultaneously with formation of the openings 70, 74, 76.

A selected photoresist film is applied to both sides of the metal plate 152. The photoresist is preferably applied using evaporation, a spin-on photoresist application method, or other method that produces a uniform and well-controlled thickness of photoresist on both sides of the stock metal plate 152.

The photoresist film is exposed to a selected light using a pattern mask in a step 156. As is known in the art, photoresist is a light-sensitive substance whose resistance to certain types of etching chemicals is altered by exposure to light. With positive photoresists, exposure to light weakens resistance to the chemical etching. With negative photoresists, exposure to light strengthens resistance to the chemical etching.

Interposing the pattern mask between the light and the photoresist film during the exposure step 156 causes selective exposure of the photoresist film. For a positive photoresist, the pattern mask blocks exposure except in the areas to be etched, i.e. the openings 70, 74, 76. For a negative photoresist, the mask blocks exposure only in the areas to be etched, i.e. the openings 70, 74, 76.

The pattern mask is preferably constructed from a computer-assisted drawing (CAD) design using known methods. The pattern mask can also be generated by photographic replication and optional reduction or enlargement of a precise and accurate manual drawing of the target light exposure pattern.

The exposed photoresist is developed in a step 158. The developing step 158 includes optional annealing or other curing of the exposed photoresist to optimize etching characteristics of the light-exposed and unexposed regions, followed by chemical etching in a developer chemical that selectively removes the light-exposed regions of the photoresist film (for positive photoresist) or the regions of the photoresist film which were not exposed to light (for negative photoresist). The developing step 158 causes the photoresist to be patterned such that those areas of the metal plate 152 which are to be removed, i.e. the openings 70, 74, 76, are not covered by photoresist, while the remainder of the metal plate 152 remains covered.

The metal plate 150 with the patterned photoresist is etched in a step 160 using an etchant that etches the metal plate 150 but leaves the developed photoresist substantially unaffected. Hence, the exposed regions of the patterned photoresist corresponding to the openings 70, 74, 76 are etched, while the photoresist-coated remainder of the metal plate 150 is left substantially unaffected.

For the preferred embodiment in which the photolithography process 150 defines the outer dimensions of the desired alignment plate 60, the photoresist pattern preferably additionally includes a continuous contour exposed region through which the etchant can cut out the alignment plate 60 in a precise and accurate fashion. Similarly, the throughholes 74 for the fasteners 100 or other features of the alignment plate 60 are suitably incorporated into the photoresist pattern and hence formed in the metal plate 150 during the etching step 160.

After the etching step 160, the developed photoresist 162 is removed in a step 162. Typically a solvent such as acetone or the like suitably removes the developed photoresist while leaving the metal substantially unaffected. It will be appreciated that a small amount of residual photoresist contamination will typically remain after the cleaning step 162. Since small amounts of residual contamination do not affect the functional use of the alignment plate 60, the photoresist removal step 162 preferably uses a solvent exposure which leaves small amounts of residue contamination remaining on one or more surfaces of the alignment plate 60. Such residual contamination can be detected, for example, using sensitive chemical surface analysis techniques such as Auger electron spectroscopy, x-ray photoemission spectroscopy (XPS), or the like.

The photoresist application, exposure, developing, metal etching, and photoresist removal steps 154, 156, 158, 160, 162 are well-known in the photolithographic arts, and the skilled artisan can select an appropriate photoresist, metal etchant, and photoresist solvent, and corresponding appropriate photolithographic parameters such the photoresist thickness, exposure time, etching time, and the like to optimize the method 150 for selected types of stock metal plates, for available photolithography facilities, and so forth.

In one suitable embodiment, although the photoresist is applied to both sides of the metal plate 152 in the step 154, the pattern-defining step 156 is applied to only one side of the metal plate 152. In this case the developed photoresist has openings only on the exposed side, and the etching step 160 etches the openings 72, 74, 76 from the exposed side.

In another suitable embodiment, the pattern-defining step 156 is applied to both sides of the metal plate 152 so that the etching step 160 etches the openings 72, 74, 76 simultaneously from both sides of the metal plate 152. This embodiment beneficially reduces the etching time by about a factor of two. However, precise relative alignment of the exposed patterns on the two sides should be achieved using known pattern mask alignment techniques, so that during the etching step 160 the simultaneously etched openings from the two opposite sides line up and properly join.

In actually constructed embodiments, the alignment plate 60 has an accuracy in hole placement that is better than 0.0025 cm across a 100 cm area. However, undercutting or other imperfections introduced during the etching step 160 may produce openings 72, 76 which are not optimally defined with respect to circularity and diameter. To improve circularity and diameter accuracy of the openings 72, 76, the openings 72, 76 are optionally mechanically reamed in a step 164 to more precisely define the shape and size of the openings. The starting stock metal plate has been found to have an optimal thickness of about 0.025 centimeters for stainless steel. Thicker plates result in reduced hole diameter accuracy, while thinner plates result in reduced mechanical strength of the alignment plate 60.

In addition to high precision and accuracy in the placement of alignment openings, those skilled in the art will recognize substantial additional advantages in using photolithography to define the alignment openings and other structures of the alignment plates 60. One particular advantage is that the manufacturing cost of the alignment plate is generally independent of the number of alignment openings formed therein. Hence, the conventional arrangement of a restricted number of anti-scatter modules which each include a plurality of anti-scatter plates is not necessary. Rather, the anti-scatter plates 80 and spacer plates 82 can be directly installed without the module-defining end caps 84.

Figure 13:
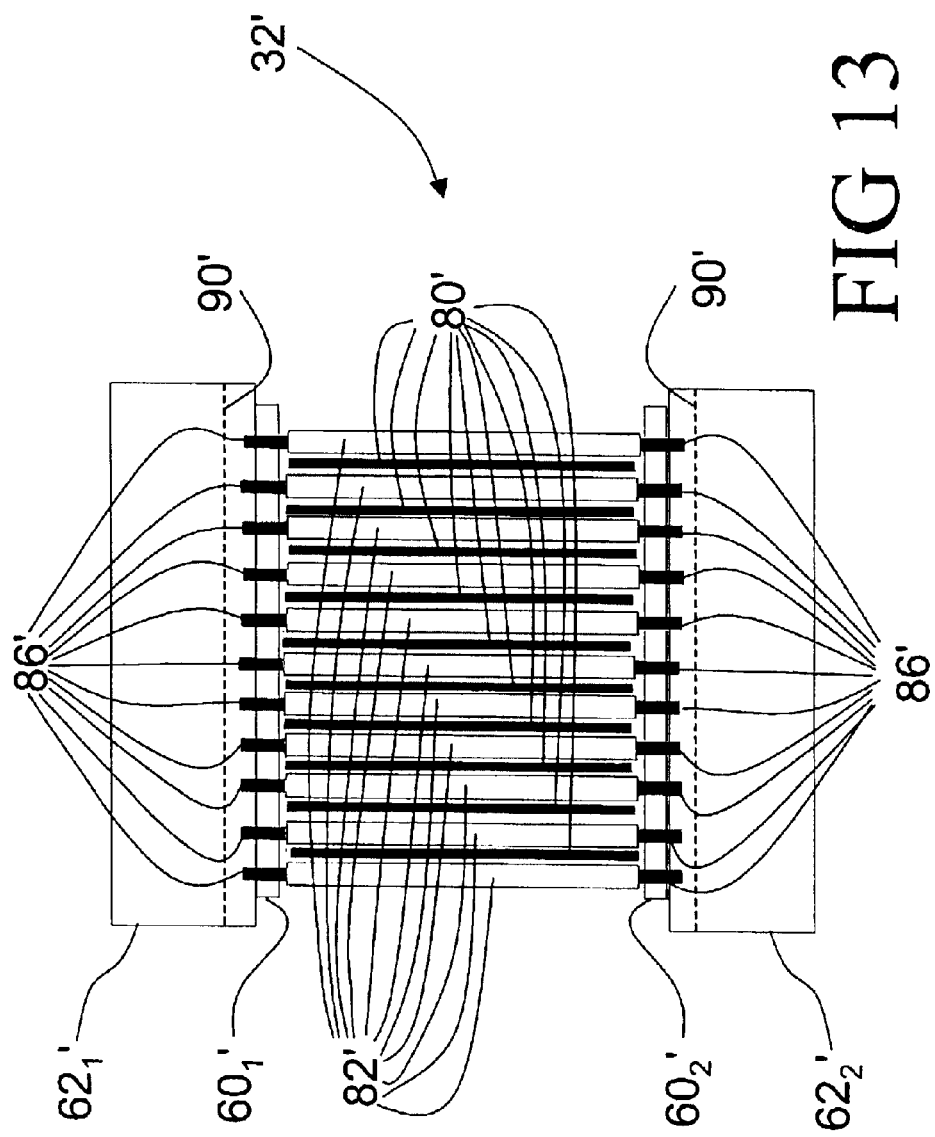
FIG. 13 shows a front view of a second embodiment of the anti-scatter element.

With reference to FIG. 13, an anti-scatter element 32' which omits the end caps 84 is described. Components of the anti-scatter module 32' that generally correspond with elements of the anti-scatter module 32 are designated by corresponding primed reference numbers herein. Spacer plates 82' are modified compared with the spacer plates 82 to include alignment nubs or pins 86' that mate with alignment openings in alignment plates $60_1'$, $60_2'$, which are modified compared with the alignment plates $60_1$, $60_2$ by including a higher density of anti-scatter alignment openings corresponding to the alignment nubs or pins 86' of the spacer plates 82'. The anti-scatter plates or vanes 80' are substantially similar to the anti-scatter plates 80, and are held between contacting spacer plates 82' frictionally or using an adhesive such as a pressure-sensitive adhesive. The support elements 62$_1$', 62$_2$' include recess troughs 90' dimensioned to provide space for the nubs or pins 86' that project through the anti-scatter plates 60$_1$', 60$_2$'.

Figure 14:
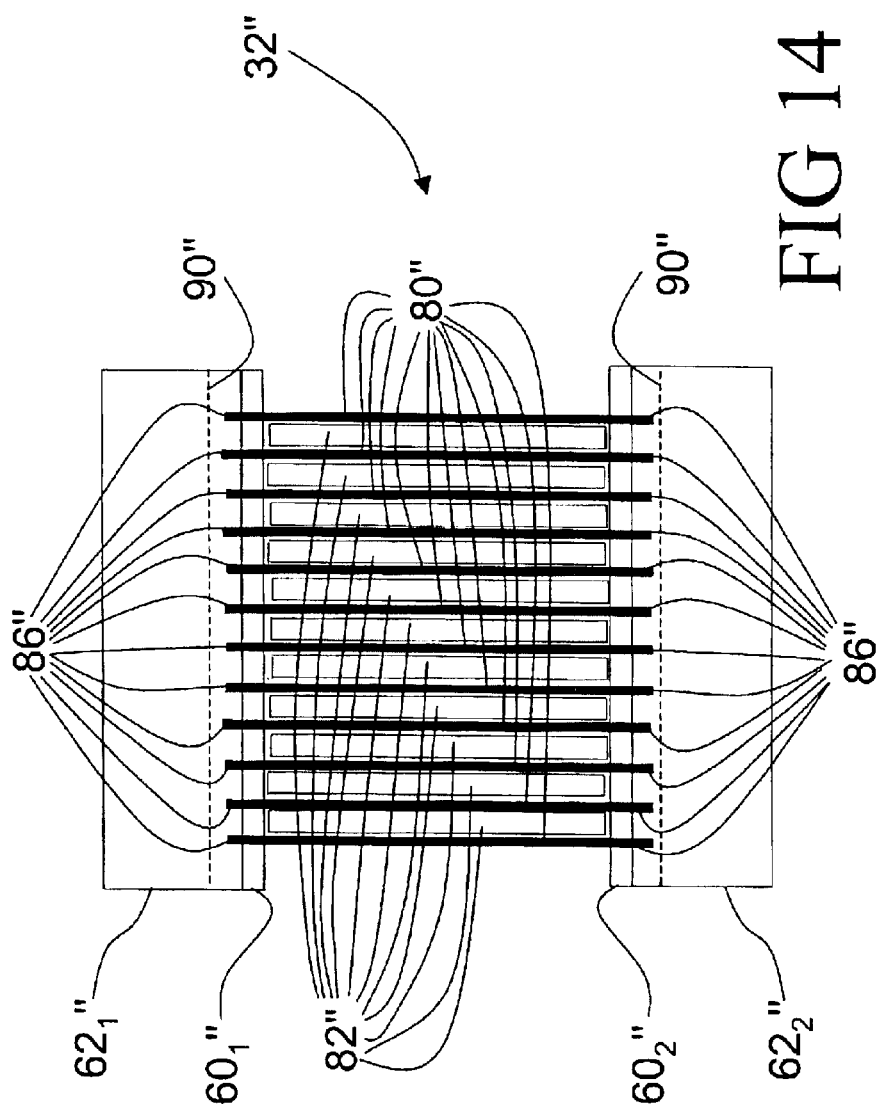
FIG. 14 shows a front view of a third embodiment of the anti-scatter element.

With reference to FIG. 14, another anti-scatter element 32" which omits the end caps 84 is described. Components of the anti-scatter module 32" which generally correspond with elements of the anti-scatter module 32 and the anti-scatter module 32' are designated by corresponding double-primed reference numbers herein. The anti-scatter plates or vanes 80" are modified compared with the anti-scatter plates 80 and the anti-scatter plates 80' to include alignment nubs, pins, or extensions 86" that mate with alignment openings in alignment plates 60$_1$", 60$_2$", which are modified compared with the alignment plates 60$_1$, 60$_2$ by including a higher density of anti-scatter alignment openings corresponding to the alignment nubs, pins, or extensions 86" of the anti-scatter plates 80". The spacer plates 82" are substantially similar to the spacer plates 82, and preferably do not include nubs or projections. The spacer plates 82" are held between contacting anti-scatter plates 80" frictionally or using an adhesive such as a pressure-sensitive adhesive. The support elements 62$_1$", 62$_2$" include recess troughs 90" dimensioned to provide space for the nubs, pins, or extensions 86" that project through the anti-scatter plates 60$_1$", 60$_2$".

In the various anti-scatter elements 32, 32', 32', it is to be appreciated that the alignment protrusions, nubs, pins, or extensions 86, 86', 86" can be cylindrical extensions, slots, or the like. The extensions 86', 86" can be correspond to extensions of the spacer plate 82' or the anti-scatter plate 80", respectively, to a length greater than the separation of the alignment plates 60', 60", such that the extensions 86', 86" are planar tabs substantially spanning a length of a side of the spacer plate 82' or the anti-scatter plate 80". In this arrangement the alignment openings of the alignment plates 60', 60" corresponding to each spacer plate 82' or anti-scatter plate 80" are single long slots each receiving a planar tab.

Although the radiation detector 30 has been described with reference to a computed tomography imaging scanner, it is readily modified for use in other imaging systems. For example, a gamma camera for nuclear medical imaging typically includes detector arrays substantially similar to the detector array 110 with scintillators suitable for converting radiation produced by an administered radiopharmaceutical to light detectable by the detector array. Gamma cameras further typically include radiation collimators that define radial directions or narrow viewing cones corresponding to each detector element. Those skilled in the art can readily adapt the alignment plates 60, 60', 60" to precisely and accurately align collimators on a gamma camera. In such an adaptation, since the collimators of a gamma camera preferably define precisely parallel projections, the spatial focal point 34 described herein is suitably located at mathematical infinity, corresponding to precisely parallel radial lines 72. Analogously, these techniques can be applied to conventional x-ray, digital x-ray, fluoroscopy, and the like.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A two-dimensional radiation detector for a radiographic scanner, the radiation detector comprising:

a support structure;

an alignment board secured to the support structure and including photolithographically defined alignment openings arranged to define a spatial focus relative to the alignment board;

an anti-scatter module mounted on the support structure and including one or more protrusions which mate with alignment openings of the alignment board to align the anti-scatter module with the spatial focus; and a detector board including a substrate and an array of radiation-sensitive elements arranged on the substrate for detecting radiation produced by the radiographic scanner, the detector board further including alignment structures that align the detector board with the anti-scatter module.

2. The radiation detector as set forth in claim 1, wherein the radiation-sensitive elements of the detector board include:

a scintillator that produces scintillation events responsive to impingement of radiation produced by the radiographic scanner on the scintillator; and an array of photodetectors arranged to view the scintillator and detect the scintillation events.

3. The radiation detector as set forth in claim 1, wherein the anti-scatter module includes:

a plurality of anti-scatter vanes, each including one or more protrusions which mate with alignment openings of the alignment board.

4. The radiation detector as set forth in claim 1, wherein the alignment openings of the alignment board are mechanically shaped after the photolithographic definition.

5. The radiation detector as set forth in claim 1, wherein the alignment openings of the alignment board include a plurality of opening pairs, each opening pair arranged in a plane containing the paired openings and the spatial focus.

6. The radiation detector as set forth in claim 1, wherein the radiographic scanner includes:

a computed tomography scanner including an x-ray source that rotates about an examination region and emits an x-ray beam that traverses the examination region and strikes the radiation detector, the radiation detector being arranged with the spatial focus substantially coinciding with the x-ray source to detect the x-rays after traversing the examination region.

7. A two dimensional radiation detector for a radiographic scanner, the radiation detector comprising:

a support structure;

an alignment board secured to the support structure; and an anti-scatter module disposed on the support structure, the anti-scatter module including a plurality of anti-scatter vanes and spacer plates arranged between the anti-scatter vanes, the spacer plates defining a selected spacing and relative tilt between the anti-scatter vanes, the spacer plates each including protrusions which mate with alignment openings of the alignment board to align the anti-scatter module with a spatial focus.

8. The radiation detector as set forth in claim 7, wherein the anti-scatter module further includes:

adhesive arranged between each anti-scatter vane and adjacent spacer plates to secure the spacer plates to the anti-scatter vane.

9. A two-dimensional radiation detector for a radiographic scanner, the radiation detector comprising:
two substantially planar alignment boards arranged parallel to one another;
two support plates, each support plate supporting one of the two substantially planar alignment boards with the two substantially planar alignment boards arranged between the support plates;
an anti-scatter module arranged between the two substantially planar alignment boards and including one or more protrusion arranged on opposite sides of the anti-scatter module which mate with alignment openings of the two substantially planar alignment boards to align the anti-scatter module with a spatial focus; and
a detector board including a substrate and an array of radiation-sensitive elements arranged on the substrate for detecting radiation produced by the radiographic scanner, the detector board further including alignment structures that align the detector board with the anti-scatter module.

10. The radiation detector as set forth in claim 9, wherein the anti-scatter module includes:
a plurality of anti-scatter vanes formed of a material which is substantially absorbing for radiation produced by the radiographic scanner; and
two end caps disposed on opposite sides of the anti-scatter vanes and retaining the anti-scatter vanes, each end cap including one or more protrusions which mate with alignment openings of the two substantially planar alignment boards.

11. The radiation detector as set forth in claim 10, wherein the anti-scatter module further includes:
a plurality of spacer plates arranged between the anti-scatter vanes and parallel thereto that define a selected spacing between the anti-scatter vanes, the spacer plates being formed of a material which is substantially radiation-translucent to radiation.

12. The radiation detector as set forth in claim 9, wherein the alignment openings of the two substantially planar alignment boards are photolithographically defined openings.

13. The radiation detector as set forth in claim 9, wherein the alignment structures of the detector board include alignment openings, and the anti-scatter module includes detector alignment pins that insert into the detector board alignment openings to align the detector board with the anti-scatter module.

14. A method for manufacturing a radiation detector for a computed tomography scanner, the method comprising:
photolithographically defining alignment openings in an alignment board;
aligning an anti-scatter element with the alignment board by mating one or more protrusions of the anti-scatter element with a selected one or more of the alignment openings of the alignment board; and
aligning and mounting a detector board with the anti-scatter element, the detector board including a substrate and an array of radiation-sensitive elements arranged thereon.

15. The method as set forth in claim 14, wherein the step of defining alignment openings in an alignment board further includes mechanically reaming the photolithographically defined alignment openings to improve at least one of a size and a circularity of the openings.

16. The method as set forth in claim 14, wherein the photolithographic defining of alignment openings in an alignment board includes:
photolithographically defining an edge of the alignment board.

17. The method as set forth in claim 14, wherein the photolithographically defined alignment opening are arranged to define a spatial focal point relative to the alignment board, and the aligning of the anti-scatter element on the alignment board includes:
aligning a plurality of anti-scatter elements on the alignment board with each anti-scatter element aligned to selectively pass radiation originating at the spatial focal point.

18. The method as set forth in claim 17, wherein the radiographic scanner includes an x-ray source on a rotating gantry that produces x-rays which pass through an examination region and strike the radiation detector, the method further including:
mounting the radiation detector onto the computed tomography scanner, including aligning the spatial focal point defined by the alignment openings with the x-ray source.

19. The method as set forth in claim 14, further including:
repeating the steps of aligning an anti-scatter element and aligning and mounting a detector board for a plurality of anti-scatter elements and detector boards.

20. The method as set forth in claim 14, wherein the step of aligning and mounting a detector board includes:
mating an alignment structure of the detector board with a corresponding alignment structure of the anti-scatter element.

21. The method as set forth in claim 14, wherein the anti-scatter element includes a parallel array of radiation-absorbing plates, and the step of aligning a detector board includes;
arranging the radiation-sensitive elements between adjacent radiation-absorbing plates.

22. The method as set forth in claim 14, further including:
securing the alignment board to a support structure, the securing including aligning the alignment board with the support structure using selected alignment openings of the alignment board.

23. A method for manufacturing a radiation detector for a computed tomography scanner, the method comprising:
photolithographically defining alignment openings in two alignment boards to produce two interchangeable alignment boards each having alignment openings; and
aligning an anti-scatter element with the alignment boards by arranging the two interchangeable alignment boards parallel to one another with a selected gap therebetween, and mating protrusions on opposite sides of the anti-scatter element with alignment openings of the two parallel alignment boards to align the anti-scatter element in the selected gap between the alignment boards.

24. A method for manufacturing a radiation detector for a computed tomography scanner, the method comprising:
applying a photoresist film to an alignment board;
exposing and developing the photoresist film to define openings in the developed photoresist film that correspond to the alignment openings;
etching the alignment board with the developed photoresist to define the alignment openings;
removing the developed photoresist;
aligning an anti-scatter element with the alignment board by mating one or more protrusions of the anti-scatter element with a selected one or more of the alignment openings of the alignment board; and aligning and mounting a detector board with the anti-scatter element, the detector board including a substrate and an array of radiation-sensitive elements arranged thereon.

25. The method as set forth in claim 24, wherein the step of applying a photoresist film to the alignment board includes applying a photoresist film to two opposite sides of the alignment board.

26. A radiographic scanner comprising:

a support frame;

a radiation source mounted to the support frame which emits a diverging radiation beam from a focal region;

first and second interchangeable generally symmetrical, substantially planar alignment boards arranged parallel to one another with a selected gap therebetween and secured to the support frame, each alignment board including an array of alignment openings formed therein;

a plurality of anti-scatter modules each including a plurality of parallel radiation-absorbing plates, the anti-scatter module arranged between the alignment boards and aligned with respect to the radiation focal region by protrusions on opposite sides of the anti-scatter modules that mate with the alignment openings of the first and the second alignment boards; and a plurality of detector boards that mount to and align with the anti-scatter modules after the anti-scatter modules are mounted between the alignment boards and aligned with the focal spot regions.

27. The radiographic scanner as set forth in claim 26, wherein each anti-scatter module includes:

first a second caps that connect with opposite sides of the radiation-absorbing plates, the first cap including protrusions that mate with alignment openings of the first alignment board and the second cap including protrusions that mate with alignment openings of the second alignment board to align the anti-scatter plates with respect to the radiation focal region.

28. The radiographic scanner as set forth in claim 26, wherein the first and the second generally symmetrical, substantially planar alignment boards further include:

residue contamination on at least one surface left over from a photolithographic processing of the alignment boards.

29. The radiographic scanner as set forth in claim 26, wherein the array of alignment openings formed in each alignment board include:

a plurality of alignment opening groups, each alignment opening group defining a line aligned with an x-ray ray path.

30. The radiographic scanner as set forth in claim 26, wherein the array of alignment openings formed in each alignment boar include:

a plurality of alignment opening groups, each alignment opening group defining a radial line, the radial lines of the plurality of alignment opening groups converging at the radiation focal region.

* * * * *